US011246765B2

(12) United States Patent
Toong (10) Patent No.: US 11,246,765 B2
(45) Date of Patent: Feb. 15, 2022

(54) SMART DIAPER SYSTEM

(71) Applicant: Neurostim Solutions LLC, Waltham, MA (US)

(72) Inventor: Hoo-min D. Toong, Cambridge, MA (US)

(73) Assignee: NEUROSTIM SOLUTIONS LLC, Waltham, MA (US)

( * ) Notice: Subject to any disclaimer, the term of this patent is extended or adjusted under 35 U.S.C. 154(b) by 771 days.

(21) Appl. No.: 16/117,133

(22) Filed: Aug. 30, 2018

(65) Prior Publication Data

US 2019/0117468 A1 Apr. 25, 2019

Related U.S. Application Data

(60) Provisional application No. 62/576,755, filed on Oct. 25, 2017, provisional application No. 62/576,839, filed on Oct. 25, 2017.

(51) Int. Cl.
*A61F 13/42* (2006.01)
*G06Q 30/06* (2012.01)
*A61F 13/84* (2006.01)

(52) U.S. Cl.
CPC .............. *A61F 13/42* (2013.01); *A61F 13/84* (2013.01); *G06Q 30/0635* (2013.01); *A61F 2013/424* (2013.01); *A61F 2013/8482* (2013.01)

(58) Field of Classification Search
CPC .............. A61F 13/42; A61F 2013/8482; A61F 2013/424; A61F 13/84; G06Q 30/0635
See application file for complete search history.

(56) References Cited

U.S. PATENT DOCUMENTS

| 7,643,874 B2 | 1/2010 | Nitzan et al. |
| 7,689,285 B2 | 3/2010 | Garabet |
| 7,922,676 B2 | 4/2011 | Daskal et al. |
| 8,279,063 B2 | 10/2012 | Wohltjen |
| 8,319,005 B2 | 11/2012 | Becker et al. |
| 8,810,388 B2 | 8/2014 | Jacobs et al. |
| 9,402,771 B2 | 8/2016 | Carney et al. |
| 9,855,427 B2 | 1/2018 | Bennett et al. |

(Continued)

FOREIGN PATENT DOCUMENTS

| CN | 108158724 A | * 6/2018 | ............. A61F 13/42 |
| WO | 2002078513 | 2/2003 | |

(Continued)

OTHER PUBLICATIONS

Yogi A. Patel; Kilohertz Electrical Stimulation Nerve Conduction Block: Effects of Electrode Surface Area; IEEE Transactions on Neural Systems and Rehabilitation Engineering, vol. 25, No. 10, Oct. 2017.

*Primary Examiner* — Susan S Su
(74) *Attorney, Agent, or Firm* — Potomac Law Group, PLLC (57) ABSTRACT

A smart diaper system includes a diaper body adapted to be worn by a user and an absorbent pad coupled to the diaper body. The system further includes a wireless communication device fixedly attached to the diaper body and a base station device in wireless communication with the wireless communication device, the base station device configured to determine a distance between the wireless communication device and the base station device.

21 Claims, 11 Drawing Sheets

(56) References Cited

U.S. PATENT DOCUMENTS

| | | |
|---|---|---|
| 10,016,600 B2 | 7/2018 | Creasey et al. |
| 10,028,865 B2 | 7/2018 | Krasnow et al. |
| 10,342,977 B2 | 7/2019 | Raghunathan |
| 2002/0019652 A1 | 2/2002 | Silva et al. |
| 2008/0110984 A1 | 5/2008 | Uchitani |
| 2010/0152688 A1* | 6/2010 | Handwerker ........... A61F 13/42 604/361 |
| 2014/0194951 A1 | 7/2014 | Gong et al. |
| 2014/0266736 A1* | 9/2014 | Cretu-Petra ............. A61B 5/01 340/573.5 |
| 2014/0324120 A1 | 10/2014 | Bogie et al. |
| 2015/0301004 A1* | 10/2015 | Carney ............. G01N 33/0047 73/31.01 |
| 2015/0335888 A1 | 11/2015 | Demers et al. |
| 2016/0015962 A1 | 1/2016 | Maragheh et al. |
| 2017/0001003 A1 | 1/2017 | Pivonka et al. |
| 2017/0224990 A1 | 8/2017 | Goldwasser et al. |
| 2017/0333695 A1 | 11/2017 | Kaplan et al. |
| 2018/0082035 A1 | 3/2018 | Collette et al. |
| 2018/0116877 A1 | 5/2018 | Ineichen |
| 2018/0133479 A1 | 5/2018 | Bennett et al. |
| 2018/0314800 A1 | 11/2018 | Matthieu et al. |
| 2018/0318585 A1 | 11/2018 | Pfeifer |
| 2020/0069941 A1 | 3/2020 | Campean et al. |
| 2020/0069942 A1 | 3/2020 | Campean et al. |

FOREIGN PATENT DOCUMENTS

| | | |
|---|---|---|
| WO | 2009064641 A1 | 5/2009 |
| WO | 2015183620 A3 | 4/2016 |

* cited by examiner

SMART DIAPER SYSTEM

CROSS REFERENCE TO RELATED APPLICATIONS

This application claims priority to U.S. Provisional Patent Application Ser. No. 62/576,839, filed on Oct. 25, 2017, and to U.S. Provisional Patent Application Ser. No. 62/576,755, filed on Oct. 25, 2017. The disclosure of each of these applications is hereby incorporated by reference.

FIELD

This invention is directed generally to diapers, and in particular to diapers with electronic augmentation to provide various analytics.

BACKGROUND INFORMATION

A "diaper" or "disposable absorbent pad" is a type of underwear that allows the wearer to defecate or urinate without the use of a toilet, by absorbing or containing waste products to prevent soiling of outer clothing or the external environment. When diapers become soiled, they require changing, sometimes by a second person such as a parent or caregiver. Failure to change a diaper on a sufficiently regular basis can result in skin problems around the area covered by the diaper.

Diapers are primarily worn by infants, toddlers, and by children who are not yet potty trained or who experience bedwetting. Adults with incontinence also use them to prevent leaks from urination or bowel movements.

DETAILED DESCRIPTION

Smart diapers in accordance with various examples disclosed herein monitor movement and the duration of use of the diaper on the user's body and collect data over time. The collected data and the resulting analytics are used to coordinate the use and disposal of diapers with bodily function analysis. The collected data regarding diaper use can also be used to assist in the selection of different types of diapers for different use cases, such as a thinner diaper/pad for comfort and less-obtrusive wear during the day, compared to a thicker diaper for overnight use and use away from home. The collected data can also provide other analytics, including determining a posture of the user.

Further, through the collection of data as to the position of the diaper on the user's body across a span of time, and the collection of data as to the user's bladder or bowel movements across a similar coincident span of time, the occurrence of bladder or bowel activity may be correlated to the various wearing positions of the diaper and the disposal of the diaper, such that the number of diapers being used across a span of time may be reduced, and the choice of a particular style of diaper such as overnight or out of the home diaper may be optimized for the user.

Further, collection of data as to the position of the diaper on the user's body across a span of time, such as 24 hours, may show by analysis of the data a pattern of repeated trips to the bathroom even though the diaper is not replaced. Such repeated trips indicate small or non-existent urine or bowel discharges, and may indicate recurring urges to empty the bladder or bowel when emptying is not necessary. Reducing trips to the bathroom can provide substantial benefits to the user, such as by reducing interruptions to work during the workday, and reducing the danger of falls and interruptions to sleep during the night. Further, this data may be used in combination with an electrical stimulator that stimulates nerves to reduce the urge to urinate or have a bowel movement, thus reducing and/or delaying the repeated trips.

The term "smart", in general, refers to the use of memory and logic components and instructions, and may also include electronic components for communications, to generate some or all of the functionality disclosed herein.

Figure 1:
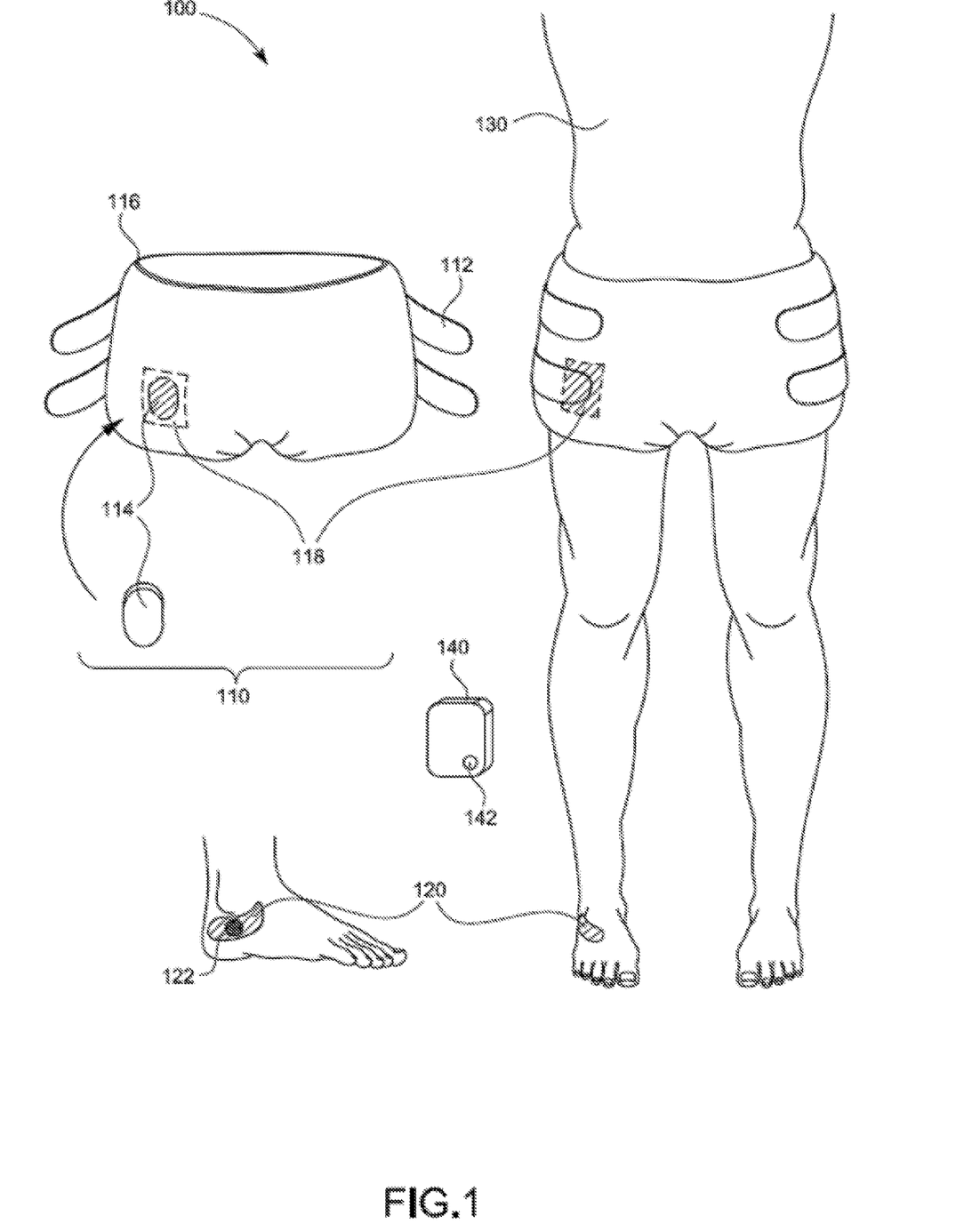
FIG. 1 illustrates an example smart diaper and data collection system.

FIG. 1 illustrates an example smart diaper and data collection system 100. System 100 includes a diaper 110 with a diaper body that includes an absorbent pad, tabs 112, a wireless beacon or monitoring device (generally, a "wireless communication device") 114 fixedly attached to the diaper body, a waistband 116 and a beacon holder 118. System 100 further includes a smart band aid or smartpad or patch 120 (hereinafter, "patch"), worn at the ankle or other fixed position, and an optional patch annunciator 122. An optional host device 140 and an optional host device annunciator 142 are further associated with a user 130. In the example of FIG. 1 and other examples disclosed below, user 130 is an adult and diaper 110 is an adult diaper.

Wireless beacon 114 can be any type of wireless communications device or monitoring device that uses wireless technology and protocols including Radio-frequency identification ("RFID"), Near-field communication ("NFC"), Wi-Fi, Bluetooth Low Energy ("BLE"), or others. Wireless beacon 114 is fixedly attached to diaper 110.

Patch 120 can be any type of device that can be fixedly attached to a user and includes a processor/controller and instructions that are executed by the processor, or a hardware implementation without software instructions, and communication elements to provide communications with wireless beacon 114. Patch 120 can also include additional components that provide topical nerve stimulation on the user to provide benefits to the user, including bladder management for an overactive bladder.

Patch 120 in one example can include a flexible substrate, a malleable dermis conforming bottom surface of the substrate including adhesive and adapted to contact the dermis, a flexible top outer surface of the substrate approximately parallel to the bottom surface, one or more electrodes positioned on the patch proximal to the bottom surface and located beneath the top outer surface and directly contacting the flexible substrate, electronic circuitry embedded in the patch and located beneath the top outer surface and integrated as a system on a chip that is directly contacting the flexible substrate, the electronic circuitry integrated as the system on the chip and including an electrical signal generator integral to the malleable dermis conforming bottom surface configured to electrically activate the one or more electrodes, a signal activator coupled to the electrical signal generator, a nerve stimulation sensor that provides feedback in response to a stimulation of one or more nerves, an antenna configured to communicate with a remote activation device, a power source in electrical communication with the electrical signal generator, and the signal activator, where the signal activator is configured to activate in response to receipt of a communication with the activation device by the antenna and the electrical signal generator configured to generate one or more electrical stimuli in response to activation by the signal activator, and the electrical stimuli configured to stimulate one or more nerves of a user wearing patch 120 at least at one location proximate to patch 120. Additional details of examples of patch 120 are disclosed in U.S. Pat. No. 10,016,600, entitled "Topical Neurological Stimulation", the disclosure of which is hereby incorporated by reference.

Host device 140 can be a smartphone or a fob, or any device with communications capability to provide communications with wireless beacon 114 and/or patch 120. Host device 140 may also include applications ("apps") or other types of user interfaces to allow a user to control wireless beacon 114 and/or patch 120.

Figure 1A:
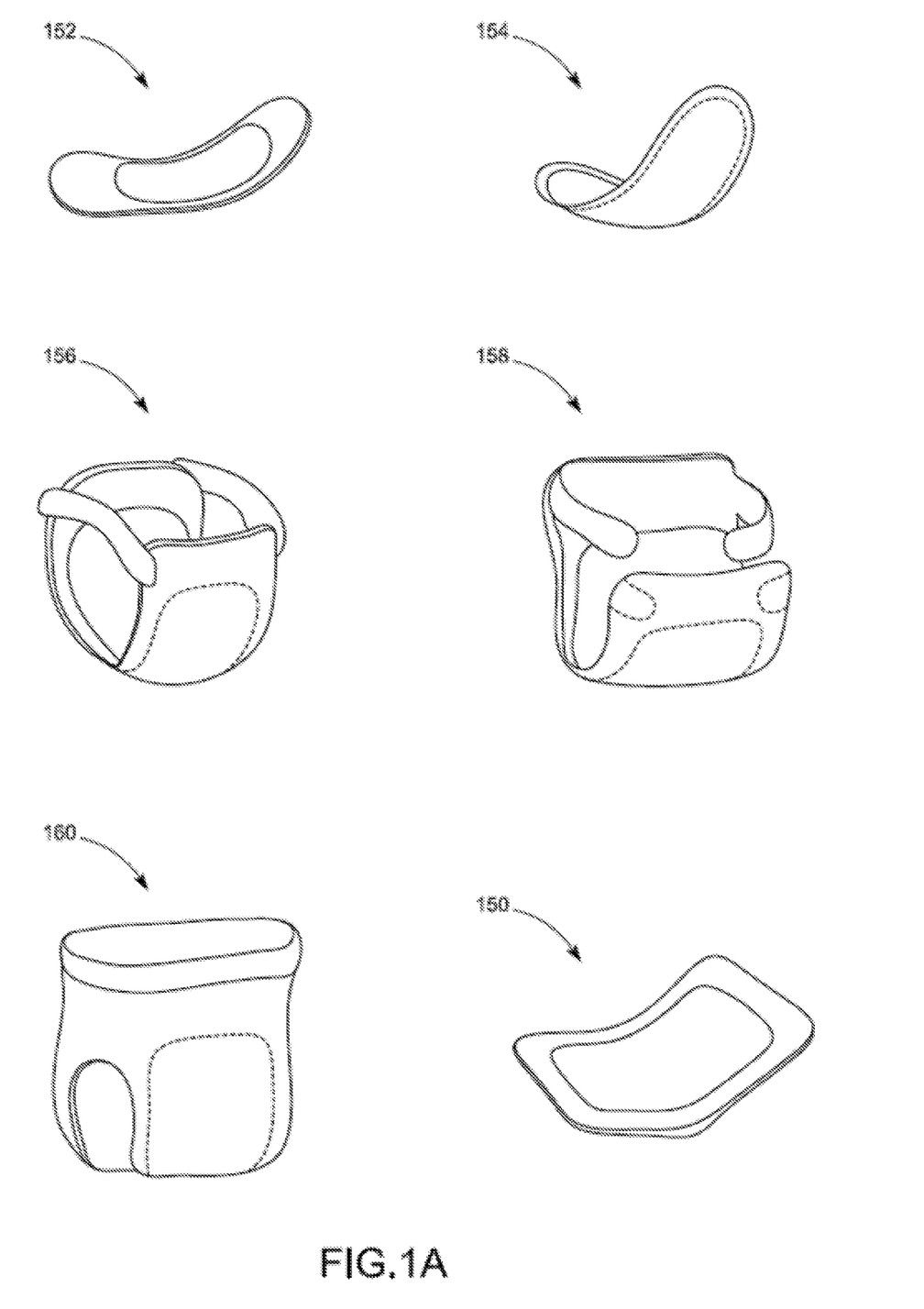
FIG. 1A illustrates other examples of disposable absorbent pads that can be used.

Diaper 110 is one example of a disposable absorbent pad used to collect urinary or bowel waste from the wearer (i.e., user 130). FIG. 1A illustrates other examples of disposable absorbent pads that can be used for diaper 110, including liner pads 150, miniature pads 152, guards 154, belted undergarments 156, pads with tabs 158, and pull-up briefs 160. Each example of FIG. 1A can include a wireless beacon 114 in a beacon holder 118 or integrated pocket, as shown in FIG. 1, that is used in conjunction with wireless beacon 114 and/or patch 120.

Figure 2:
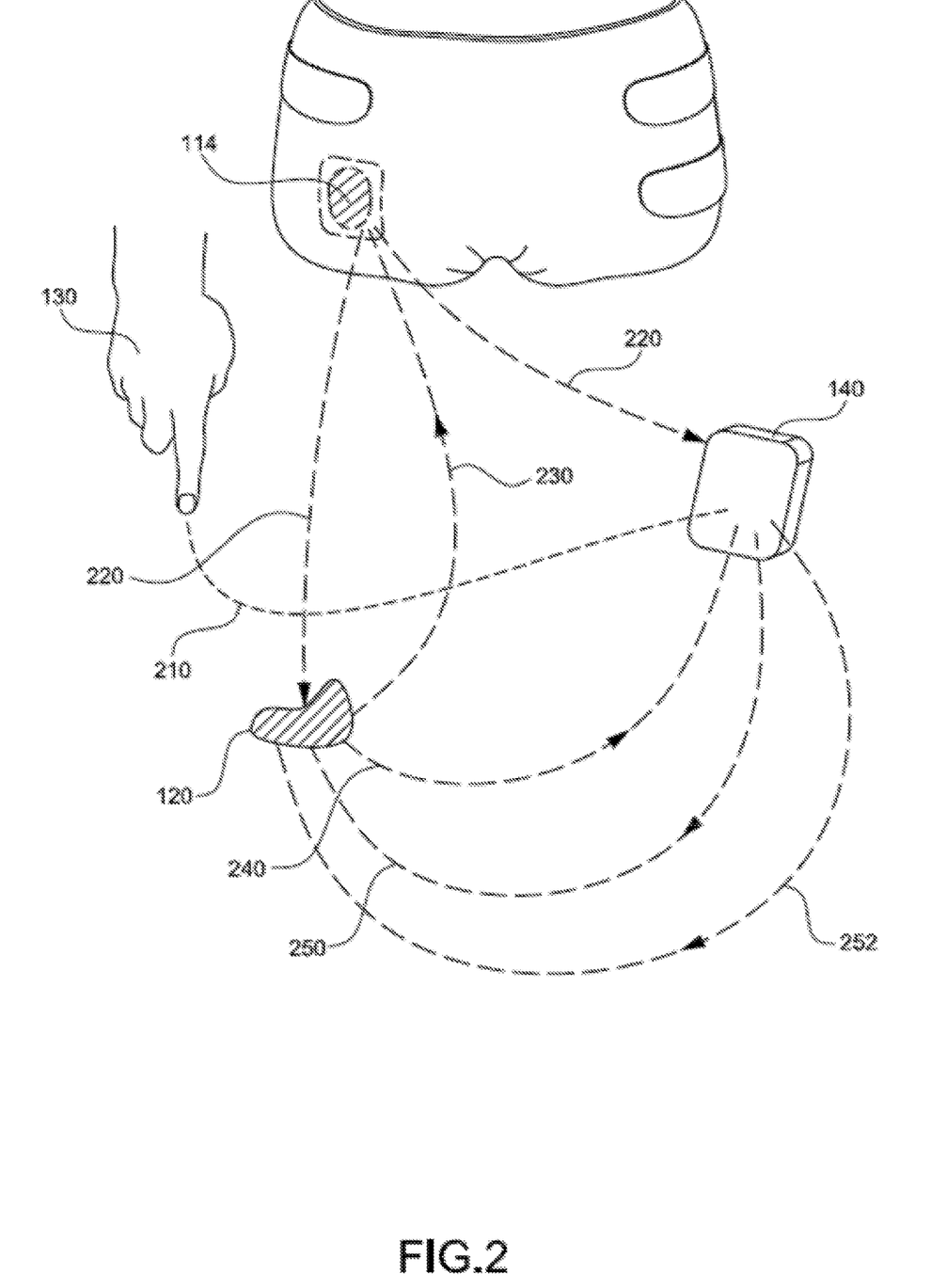
FIG. 2 illustrates various example communication signals of the data collection system of FIG. 1.

FIG. 2 illustrates various examples of communication signals of data collection system 100 of FIG. 1. The signals include a user signal 210 from user 130 to host device 140, a beacon data signal 220 from wireless beacon 114 to host device 140, a control signal 230 from patch 120 to wireless beacon 114, and a data signal 240, a host control signal 250 and a host data signal 252 between patch 120 to host device 140.

Patch 120 and beacon 114 establish communication using wireless means, such as Bluetooth based communications in all its variations, Wi-Fi, or other RF means.

In some examples, host device 140 establishes communication using wireless means with one or both of patch 120 and beacon 114.

In some examples, patch 120 controls beacon 114 using control signal 230, and beacon 114 sends data to patch 120 using beacon data signal 220.

In some examples, host device 140 controls beacon 114 using host control signal 250, and beacon 114 sends data to host device 140 using beacon data signal 220.

In some examples, host device 140 and beacon 114 are part of a larger Body Area Network ("BAN") that includes additional smart devices, such as fitness trackers, smart watches, smart phones, smart tags, and similar means.

Diaper 110 is worn by user 130 at various positions while the user is standing, including at the waist, at the thighs, at the knees, at the calves, at the feet, and separate from the body. User 130 at various positions wears diaper 110 while the user is sitting, including at the waist, at the thighs, at the knees, at the calves, and at the feet.

In some examples, data collection is performed by measuring a distance between beacon 114 and the patch 120. In some examples, data collection is performed by measuring a distance between the beacon 114 and the host device 140. In some examples, data collection is performed by measuring distances among beacon 114, the patch 120, host device 140, and other beacon equipped devices.

Data collection system 100 distinguishes the standing positions from the sitting positions in order to distinguish through measurement and analysis of the data the occurrence of a sitting event from a non-sitting event.

Data collection system 100 may be trained by user 130 to recognize specific positions/postures of the user, such as standing, sitting, lying down, with the pad in various specific positions, such as at the waist, on the thighs, at the knees, at the calves, by the user confirming via signal from the user to data collection system 100 when data collection system 100 indicates a position matching the actual position of the user. Based on the saved data, system 100 can determine a future position/posture of the user using current data of distance between beacon 114 and patch 120, or any other fixed host device.

Data collection system 100, and analytical protocols applied to the collected data, may be used to analyze patterns of behavior of the user of the diaper 110 to obtain analytics. This analysis may be used to calculate usage patterns for diaper 110, and to predict the next usage event, including but not limited to wearing a new diaper, voiding fluids or solids into a worn diaper, using a toilet after pulling the diaper down, disposing of a diaper and removing a diaper when not near a toilet.

In some examples, analysis of the data may reveal a pattern of discarding or disposing of a used diaper without events related to voiding wastes, indicating use of a diaper without soiling the pad.

In some examples diaper 110 is designed to be pulled up and down the legs as a pair of undershorts using waistband 116, so that the diaper does not include tabs 112.

In some examples, diaper 110 is designed to be wrapped around the user's body, using tabs 112 to attach the front of the diaper to the back of the diaper so that the diaper remains at the user's waist while in use. In these examples, diaper 110 may require that the tabs 112 be loosened in order that the user may move the diaper down or up the legs.

In some examples, data collection and analysis leads to improvements in selection of different types of diapers 110 for different use cases, such as a thinner diaper/pad for comfort and less-obtrusive wear during the day, compared to a thicker diaper/pad for overnight use and use away from home.

In some examples, data collection and analysis tracks diaper 110 usage to inform the user when supply of unused diaper is low, the count of unused diapers being reset to a fixed number by the user, such as when additional diapers are purchased, and the count being reduced by one each time data collection system 100 determines, through analysis of data, that a diaper 110 has been disposed of.

In some examples, diaper 110 is designed to allow the user to insert and remove beacon 114 from beacon pocket 118, beacon pocket 118 being designed to accommodate the size of beacon 114 while enclosing beacon 114 securely so that beacon 114 does not come loose from beacon pocket 118, nor does beacon 114 become inadvertently separated from the diaper 110.

In some examples, beacon pocket 118 holds a pre-installed beacon 112, the pocket not being designed to allow the user access to the enclosed beacon 112. In other embodiments, beacon 112 is integrated, disposable, and permanently attached to diaper 110.

In some examples, patch 120 and/or host device 140 collect other data, in addition to distance measurement data. Other data may include time stamps, date stamps, device power level indications, body temperature, pulse rate, circadian rhythm indicators, and other biometric data. Analysis of such data may provide correlation of movements of the diaper 110 with levels of activity, such as contrasting sleeping, eating at rest, walking, sports, and the like.

Other data may be geographical coordinates indicating the user's location while wearing diaper 110. Analysis of such data may provide correlation of movements of the diaper 110 on the body with geographical locations, such as the user's home, the user's place of work, travel long distances away from home, and the like.

Analytical protocols in patch 120 and/or host device 140 determine the position of beacon 114 and the position of diaper 110 relative to the position of patch 120 or the position of host device 140 or both, to process position data. Analytical protocols may process a series of position data to determine patterns in the measured values, thereby deriving dependable indications of diaper 110 positions.

In some examples, if patch 120 detects intermediate distances to beacon 114, such as the sitting thigh position, or the sitting knee position, patch 120 may prompt the user, such as through annunciator 122 or host device annunciator 142, to push diaper 110 further down or pull it further up so that the distance and inferred position is not ambiguous as to correlation with using the toilet.

When the user carries host device 140 with them in a repeatable location, such as a shirt pocket, then the distance from host device 140 to beacon 114 may be predictable according to the relative location of diaper 110 to host device 140.

When host device 140 is installed in a fixed location, such as a power outlet near the user's toilet, host device 140 can communicate in coordination with patch 120 on the user's body, the data collection system annotating the distance measurements with the location information from the fixed host device. The data analysis protocols may use these annotations to filter out user position information from the bathroom from user position information from other rooms, such as sitting with diaper 110 pulled down in the bedroom while changing clothing.

In some examples, host device 140 is an element of an appliance such as an air freshener, which the user plugs into a power outlet in the bathroom. In some examples, the beacon 114 has an integral battery. In some examples, the beacon 114 has no integral battery, deriving the power to reply to the measurement signal from the measurement signal itself.

In some examples, BLE protocol is used to communicate between the patch 120 and beacon 114, or between host device 140 and beacon 114, or both, since BLE is able to estimate distance between two BLE-equipped objects to a sufficient accuracy adequate for this application.

In some examples, more than one beacon 114 may be placed in diaper 110 at various distinct locations to increase the reliability of the measurement path through redundancy.

In some examples, more than one patch 120 may be placed within range of beacon 114 to increase the accuracy and reliability of the measurement path, such as wearing one medial patch 120 on the forearm and wearing a tibial patch 120 at the ankle, each having connection to the others to coordinate distance data and to make a determination of the diaper 110 position.

In some examples, system 100 may include a set of diapers, one diaper 110 having a pre-installed beacon 114, but such beacon 114 being removable from diaper 110 after the diaper is used and before the diaper is discarded, such that the beacon 114 may be installed by the user in the next diaper in the set of diapers, this re-installation process including one or more steps such as pressing of a button on beacon 114 to reset it each time it is installed or attached to a new diaper. This example system optimizes the use of one beacon 114 across a set of diapers 110 without reducing the efficacy of beacon 114 as it is reused. Reuse of beacon 114 reduces the number of disposed beacons 114, and reduces the impact to waste management and recycling.

In some examples, system 100 may include diapers with no included beacon 114, the beacon 114 being acquired separately by the user, such as through concurrent purchase with the diapers. The purchased diapers are diapers which are designed with a beacon holder 118 to accommodate a variety of beacons 114 of various sizes, such that the separately acquired beacon may be inserted by the user before using the diapers. In some examples, a set of beacons 114 may be acquired separately from the set of diaper; each beacon 114 designed to be used in one and only one diaper and then discarded. In some examples, one beacon 114 may be acquired separately from the set of diapers, the beacon 114 to be reused by the user in a series of diapers up to a maximum number of reuses.

In some examples, system 100 may include diapers which are not specifically designed for use with a beacon 114 with beacon 114 being acquired separately and fixedly attached to one or more diapers in succession through the use of a clip or adhesive or the like.

In some examples, beacon 114 is activated when diaper 110 is removed from its outer packaging, this activation being triggered by the removal of the outer packaging. In some examples, beacon 114 is deactivated when its power source is depleted, such as a battery with insufficient power remaining to power the beacon.

Beacon 114 may also be modified and applied to other locations on the diaper for purposes of being detected at a specific distance by patch 120 and/or the host device 140.

In some examples, the present invention may be used in trial situations with a limited user set, for the purpose of improving use of monitoring devices and/or adult diapers or both. In some examples, the present invention may be mass-produced to be distributed by caretakers to users, to improve the use of adult diapers for users.

In some examples, the present invention may be mass-produced to be purchased and used in a public marketplace, to improve the use of adult diapers for users.

Figure 3:
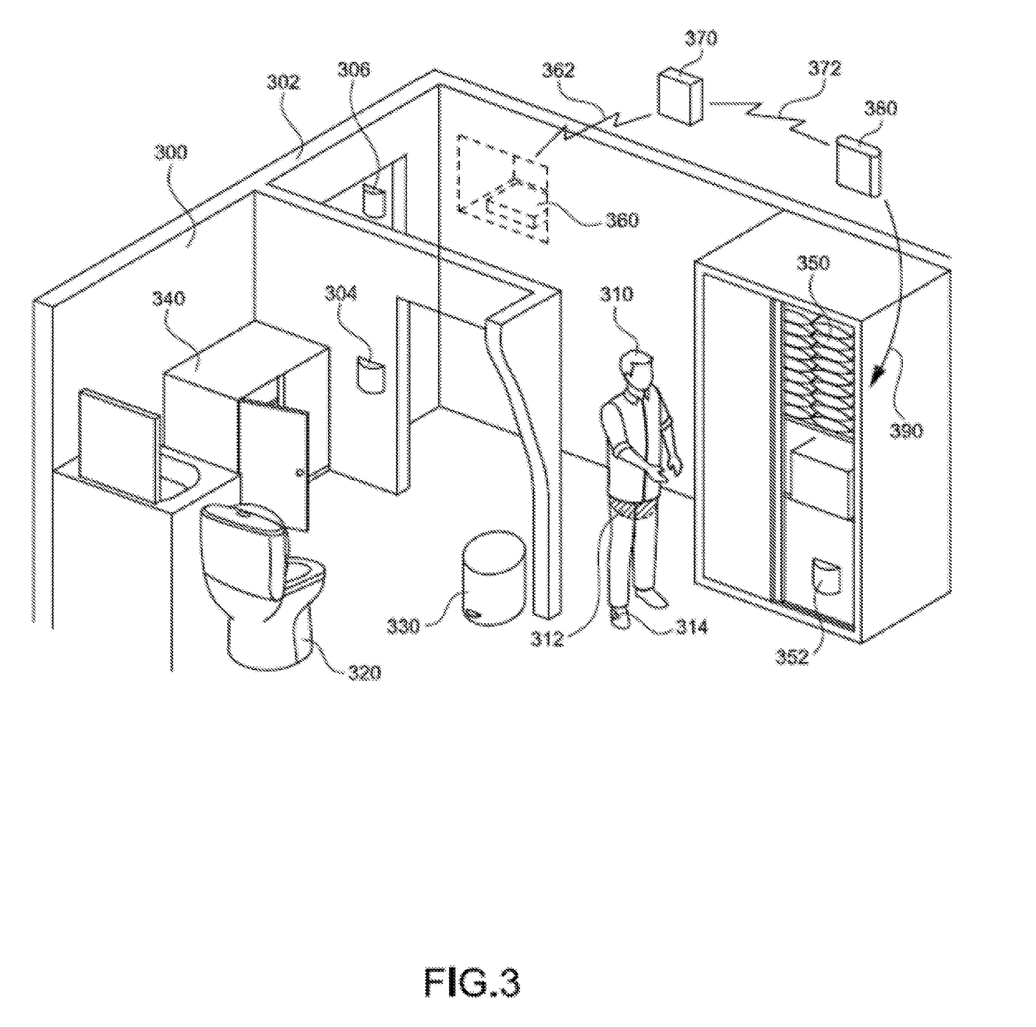
FIG. 3 illustrates an example environment for use with the system of FIG. 1.

FIG. 3 illustrates an example environment for use with system 100. As shown in FIG. 3, data from a user 310 wearing a diaper-with-beacon 312 and a patch 314 is used on coordination with data collected when user 310 is in a bathroom 300, a bedroom 302 or other rooms in the user's living space. When user 310 is in bathroom 300 or bedroom 302 or other spaces, the position of user 310 and diaper-with-beacon 312 relative to patch 314 is monitored as described, and this information is related to a bathroom monitoring appliance 304 and a bedroom monitoring appliance 306 through a wireless protocol such as BLE, sending the data to a collection hub 360. Additional monitoring appliances, such as a local supply cabinet 340, monitoring appliance 304 and the supply closet 350 monitoring appliance 352 tracks the user's movements.

Disposal of the diaper-with-beacon 312, such as into disposal can 330 is recorded by patch 314, the data then being sent to collection hub 360. As a new diaper-with-beacon 312 is taken from supply cabinet 340 or supply closet 350, or other inventory location, and worn on the user's body, the action of wearing the diaper-with-beacon 312 is recorded by patch 314, the data for this event being sent to collection hub 360. Collected data is transmitted via wired or wireless means 362 to a local server 370 such as in the office space of an institution.

Extended collected data is transmitted via wired or wireless means 372 to a remote server 380. The inventory fulfillment system associated with or connected to local server 370 or remote server 380 then triggers the delivery of additional inventory/quantity 390 of diapers-with-beacons 312 to resupply storage closet 350. Analysis of derivations optimizes the reordering of pad supplies.

Figure 4:
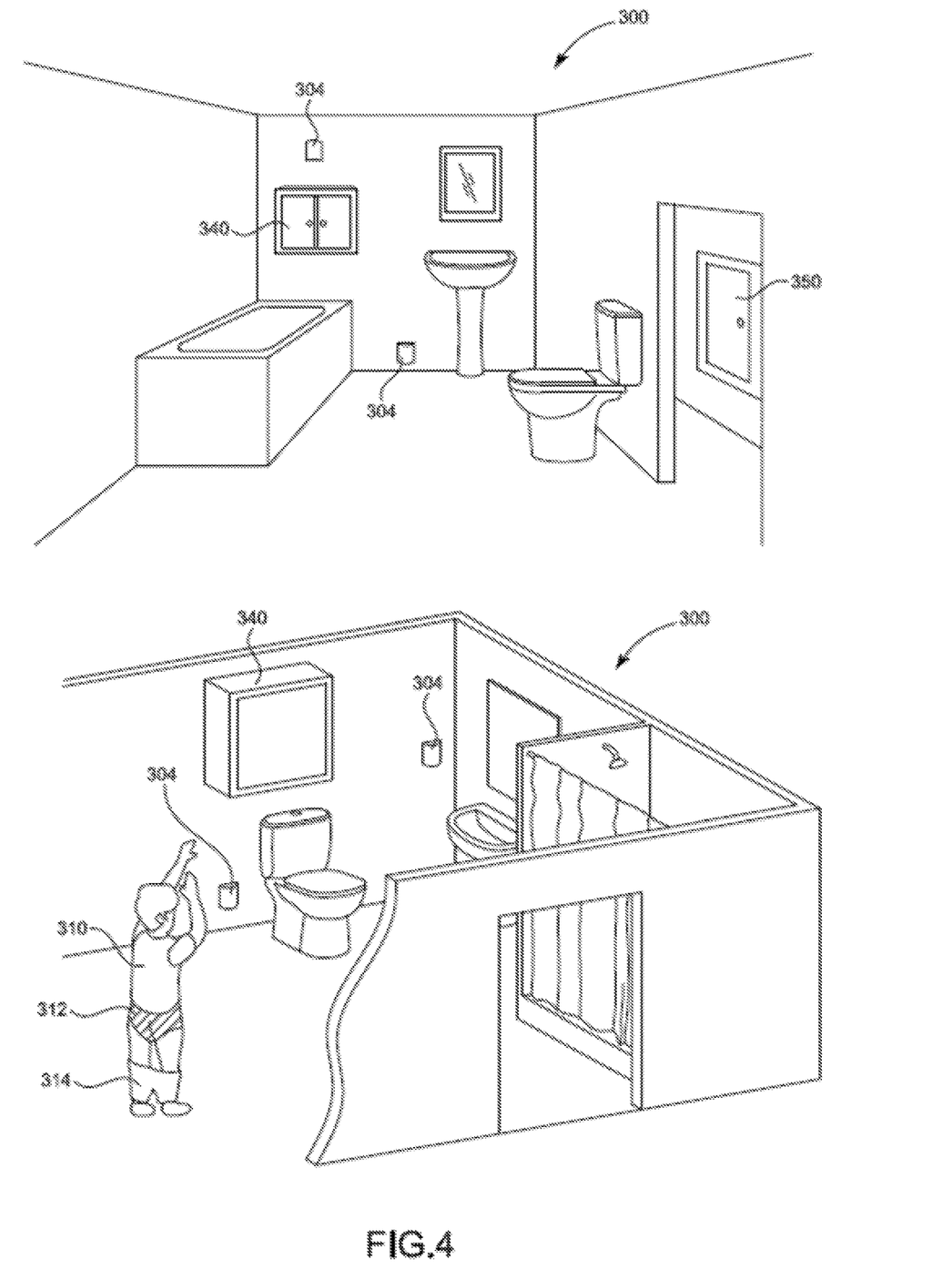
FIG. 4 further illustrates an example environment for use with the system of FIG. 1.

FIG. 4 further illustrates an example environment for use with system 100. As shown in FIG. 4, the position of diaper-with-beacon 312 on user 310 may be determined with additional accuracy by using multiple bathroom monitoring appliances 304 arranged within the bathroom 300 or other rooms in the user's living space, such that the combination of measured distances among these monitoring appliances 304 and diaper-with-beacon 312 and patch 314 provides data establishing unique absolute distances, or ratios of distance, or a combination of absolute and relative measurements which are then processed by analytical means. The locations of these multiple bathroom monitoring appliances 304 may be selected to take into account the dimensions and arrangement of the bathroom and its appliances, such as sink, toilet, shower, tub, and others. Monitoring devices may also include Bluetooth toothbrushes, Bluetooth air fresheners (plugged into the wall), or dedicated Bluetooth beacons.

In some examples, the user is able to choose the combination of different types of diapers 110 to be ordered or re-ordered when the diaper inventory 390 quantities fall below a minimum limit, thus providing the user an individualized service which establishes a relationship between the user and the supplier or suppliers, as well as restocking the inventory efficiently. This relationship, particularly with a single supplier who can fulfill the order for all requested types of diapers, is beneficial to the user in providing the user with familiar products, discounted offers, special delivery choices, and similar benefits, and beneficial to the supplier in providing access to a satisfied user for ongoing orders and as a customer for future products.

In some examples, wireless beacon 114 may be inserted into a variety of diaper types used in the course of a day or week or similar period by a user, the identity of each wireless beacon 114 being unique such that data collection system 100 may count the number of diapers of each type used by the user. Patterns of usage may be discerned by data analysis, such as particular diaper types for particular times of the day, particular user behaviors including exercising, sleeping, traveling and particular dietary changes. Resupply of diaper inventory 390 may be improved by analysis of particular diaper type usage, including anticipating diaper usage according to future events, such as dietary changes, health changes, travel plans, etc.

In some examples, resupply of inventory 390 may be effective when a centralized inventory is tracked for the usage of diapers-with-beacons by a group of users, such as in an institution such as a senior living center. Correlation of diaper type usage per individual may be integrated numerically across the group of users to anticipate inventory demands of all diaper types in use.

In some examples, the ongoing measurement of diaper 110 usage, transmitted to and collected by remote server 380, and analysis of the data, may provide one or more of the manufacturer and the distributor and the retailer of the diapers 110 to improve the selection of diaper types in their manufacturing line or inventory or on store shelves, according to the aggregate usage data.

The system of diapers-with-beacon 312 working in combination with the collection of data to servers and analysis of that data by diaper 110 providers may allow a change in behavior of the user by changing from refilling their diaper inventory by purchases at a local shop or online to an automated refilling process through the provider. In some examples, the user may opt-in to such an automated refilling system.

Figure 5:
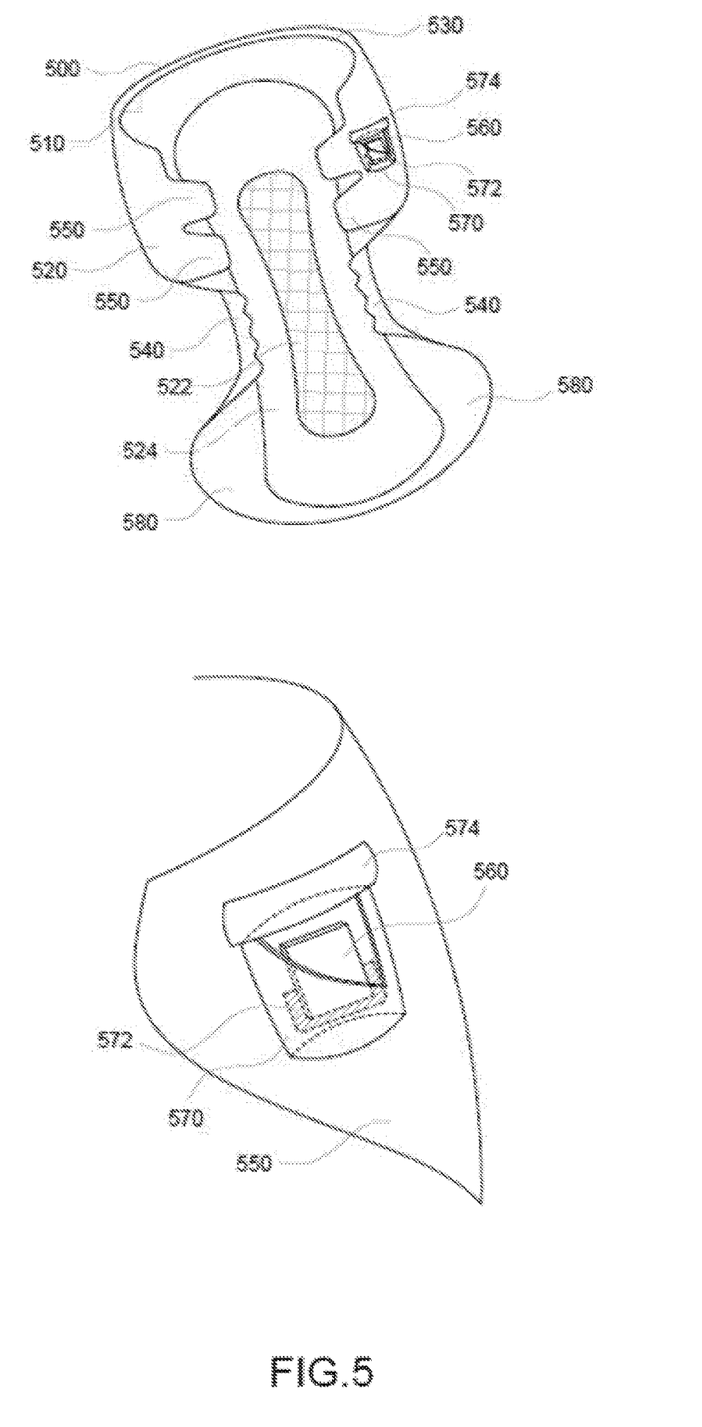
FIG. 5 illustrate another example smart diaper.

FIG. 5 illustrates another example smart diaper 500. Diaper 500 includes a body 510, an external layer 520, a primary acquisition layer 522, an absorbent layer 524, a waistband 530, leg gathers 540, tabs 550, an electronic monitoring device or wireless beacon 560, a device pocket 570 with a device pocket catch 572, a device pocket flap 574 and front wings 580. Device pocket 570 is designed to hold monitoring device 560 securely, and device pocket 570 is positioned on diaper 500 to be comfortable for the user in all positions of the user's body in normal wear, while also providing convenient access to device pocket 570 through device pocket flap 574 when diaper 500 is designed with a user-removable monitoring device 560. Monitoring device 560 and device pocket 570 are positioned on diaper body 510 so as to be protected from wetting of other parts of diaper body 510, whether through external layer 520 or through absorbent layer 524.

In some examples, diaper 500 encloses the waist of the user and is pulled up and down the legs as a pair of undershorts, the diaper therefore having no tabs 550.

In some examples, diaper 500 is designed to allow the user to insert and remove monitoring device 560 from device pocket 570 by opening device pocket flap 574 and securing monitoring device 560 to device pocket catch 572 when inserting the monitoring device, and detaching monitoring device 560 from device pocket catch 572 when removing the monitoring device.

In some examples, device pocket 570 is designed to not be opened by the user, and therefore has no device pocket catch 572, and no device pocket flap 574, the device pocket 570 fully enclosing monitoring device 560.

Figure 6A:
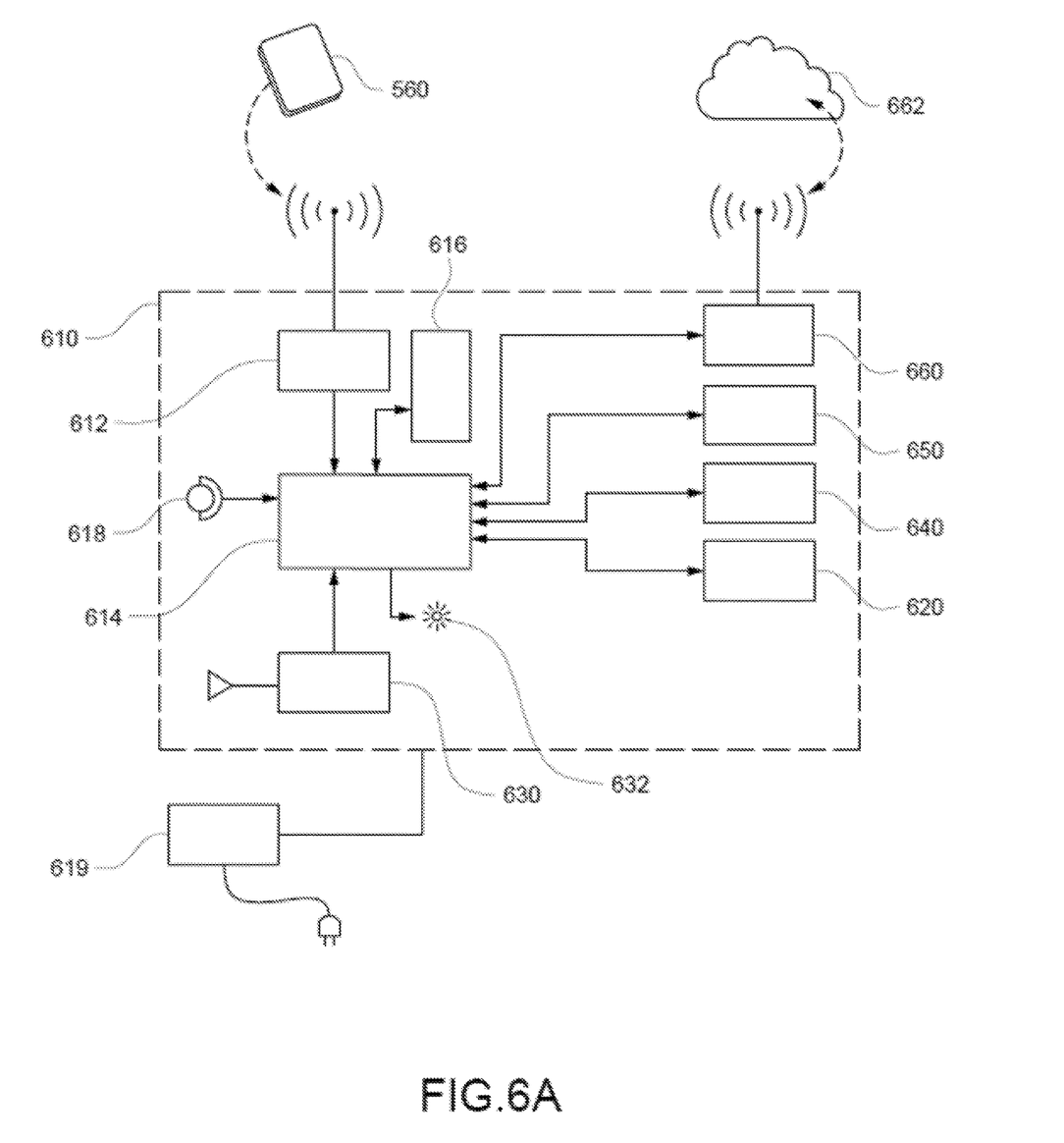
FIG. 6A is a block diagram of an example base station device in communication with a monitoring device.

FIG. 6A is a block diagram of an example base station device 610 in communication with monitoring device 560. Monitoring device 560 communicates to base station device 610 using a base station data radio 612. Base station 610 includes a base station processor 614, a base station data memory 616, a base station enabling button 618, a base station power source 619, a data collection memory 620, a base station position indicator 630, an annunciator 632, an analysis processing device 640, a data archiving memory 650, and a cloud communication device 660 to provide communications to cloud memory 662. In some examples, annunciator 632 emits one or more of a visual signal, an audible signal or a vibration signal to the user.

Monitoring device position data, and other data, flows from monitoring device 560 via base station data radio 612 to base station device 610. Base station position data, and other data, flows from base station position indicator 630 to base station device 610. In base station device 610, the data from monitoring device 560 and from base station position indicator 630 is processed by analysis-processing device 640, under control of base station processor 614, and then is stored in memory. This memory may be any combination of base station data memory 616 and data collection memory 620 and data archiving memory 650 and cloud memory 662, data movement being coordinated by base station processor 614 according to the required use of the data. Data being of immediate use is stored in base station data memory 616. Data being of periodic on-device use is stored in data collection memory 620. Data being of occasional on-device use is stored in data archiving memory 650. Data is stored in cloud memory 662 for access by other devices through a network or other means.

Other data may include time stamps, date stamps, device power level indications, body temperature, pulse rate, circadian rhythm indicators. Analysis of such data may provide a correlation of movements of diaper 500 with levels of activities, such as contrasting sleeping, eating at rest, walking, sports, and the like.

Base station 610 is powered by base station power source 619.

Position data is processed by analysis-processing device 640 to determine the position of monitoring device 560 and the position of diaper 500 relative to the position of base station device 610. Analysis of pad position and use data is used to determine patterns of use.

Figure 6B:
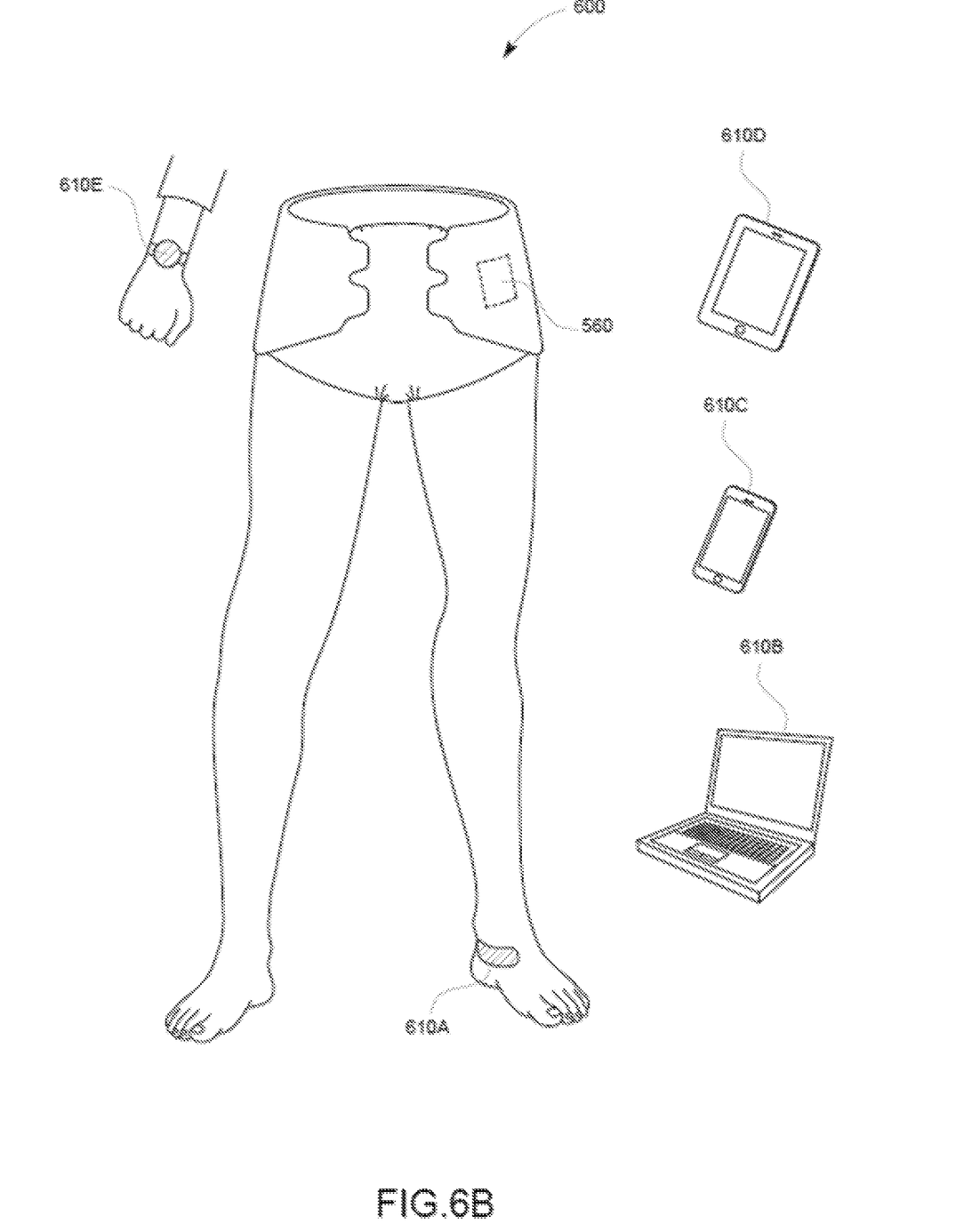
FIG. 6B illustrates an example smart diaper and data collection system.

FIG. 6B illustrates an example smart diaper and data collection system 600. In FIG. 6B, data collection system 600 includes base station 610 and monitoring device 560. The base station is one or more of a patch base station 610A, such as patch 120 of FIG. 1, a custom base station 610B, a smartphone base station 610C, a smart pad base station 610D, and a smart watch base station 610E. Each of 610A through 610E includes some or all of the elements previously described in conjunction with base station 610 in FIG. 6A. Further, in the example using patch base station 610A, patch 610A can include one or more of the elements described in conjunction with patch 120, and vice versa.

Figure 7A:
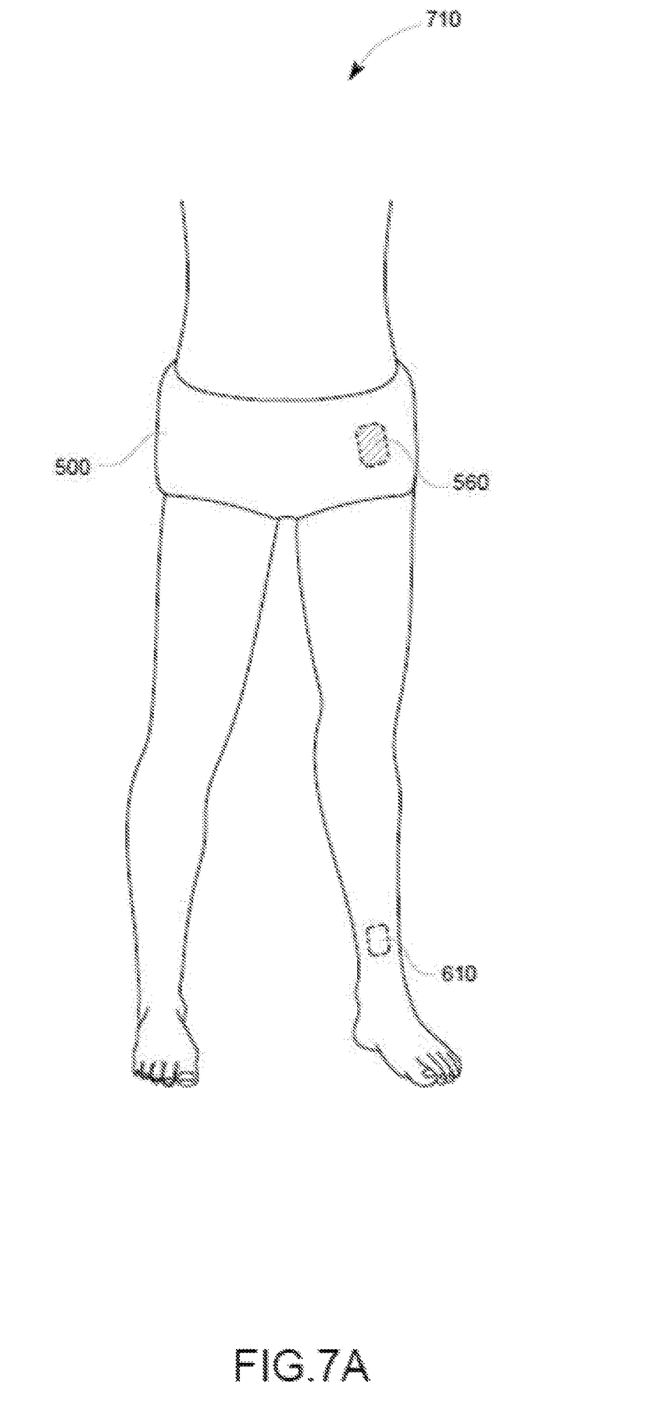
FIG. 7A illustrates a standing user with a diaper pulled up to the waist position, with monitoring device positioned relative to base station.

FIG. 7A illustrates a standing user with diaper 500 pulled up to the waist position 710, with monitoring device 560 positioned relative to base station 610.

Figure 7B:
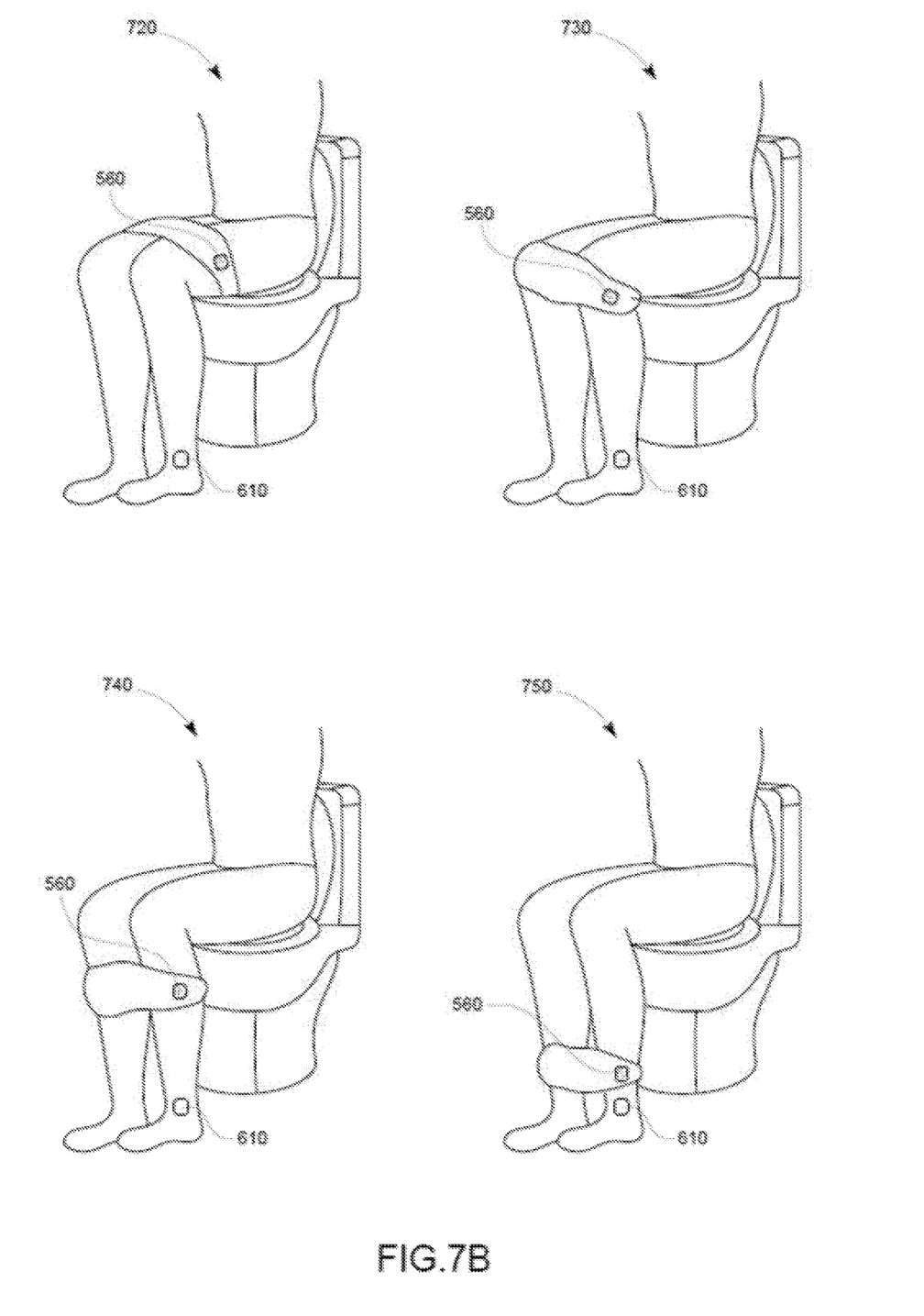
FIG. 7B illustrates four positions of the monitoring device relative to the base station.

FIG. 7B illustrates four positions of monitoring device 560 relative to base station 610. Specifically, the seated user with diaper 500 pulled down to the thigh position 720; the seated user with diaper 500 pulled down to the knee position 730; the seated user with diaper 500 pulled down to the calf position 740; and the seated user with diaper 500 pulled down to the feet position 750. All of these positions can be detected through the communication interaction between monitoring device 560 and base station 610.

In some examples, if base station 610 detects intermediate distances to monitoring device 560, such as the thigh position 720 or the knee position 730, base station 610 may prompt the user, such as through annunciator 632, to push diaper 500 further down or pull it further up so that the distance and inferred position is not ambiguous as to correlation with using the toilet.

When the user carries base station device 610 with them in a repeatable location, such as a shirt pocket as for custom base station 610B or patch base station 610C or smart phone base station 610D, or the user wears base station device 610 on their person, such as patch base station 610A or smart watch base station 610E, then the distance from base station device 610 to the monitoring device 560 will be predictable according to the relative location of diaper 500 to base station device 610.

In some examples, the analysis is simplified by using information input from the user of diaper 500, this information being input into base station device 610 to indicate to the base station to retrieve sensor position data from monitoring device 560 at various positions of the first use of diaper 500, such as the pulled-up and waist position 710, and the sitting and feet position 750. After the user confirms to base station processor 610 each of the distances corresponding to multiple positions, base station processor 610 can operate with measured distances from monitoring device 560.

Using disclosed examples, notifications of diaper use, bathroom use, such as when user enters bathroom, uses toilet, etc., may be sent to a third party such as a relative or a caregiver.

Each Bluetooth device that communicates with beacon 114 or monitoring device 560 can respond to a "ping" and offer a "service." Bluetooth device categories may be registered online, vendor-non-specific, etc.

Examples of behavior modification of the user, which may result from data monitoring, is to use fewer diapers. Further, where patch 120 is a neural stimulator, the data may inform patch 120 to perform stimulations at times of the day when a diaper change is recorded. For example, if diapers are being changed more frequently than is the norm, then the system assumes a leak is occurring. To forestall the leaking, a stimulation may defer urination. This means the use of fewer diapers. An app, for example on a smartphone or fob, may also inform the user directly to go and use the toilet before an anticipated urge occurs.

A discarded diaper may be added to the "used diaper list" in the software. The app (i.e., software) makes this determination when it sees a previously worn diaper's location move far away from the user. When that distance exceeds the "body length", then the software assumes the diaper has been left behind/discarded. It is not necessary for the user to immediately unpack and put on a new diaper for that new diaper to replace the old diaper's "wearing this now" status. The user may not put on a new diaper immediately, but the app provides valuable data by recording "I took off a diaper" as described above. The user may also be instructed to touch a button or other means in the app, whenever they change a diaper.

Devices around the bathroom or other room may be added by the user. When a new device is detected by the app or fob or directly by the patch, it is useful to know the type of device. The app prompts the user to select the new device's "type" and "brand" in the app itself using, e.g., drop-down menus. Further, a caregiver or other person can make the same entries on behalf of the user, then hand the phone or fob back to the user.

As disclosed, examples determine a distance between beacon 114 and patch 120, as well as a distance in some examples between patch 120 and host device 140, which may be a fob, smartphone, or other base station devices as shown in FIG. 6B. In a fob example, the distance is determined using BLE and the Received Signal Strength Indicator ("RSSI"). The Fob will attempt to pair with a patch 120 it detects with the strongest RSSI signal, only if the patch is within 2 feet or some other predefined distance.

After the fob pairs with a patch, that connection is "latched". The fob will pair with no other patch. The patch will pair with no other fob. Each device "remembers" the unique ID of the device with which it is paired.

If the BLE connection is broken, the fob will attempt to pair again, yet only complete a pairing with the patch it had immediately before.

Other patches that may reply to the "ping" of the fob searching for its partner will not be recognized by the fob software.

The fob pings the patch periodically as a kind of "heartbeat" to make sure that the patch is still there. Therefore, the fob knows within a margin of error that the patch is still there. This avoids the fob having to initiate a new pairing when the user presses the START button for a stimulation (i.e., when patch 120 provides neural stimulation). The stimulation can begin immediately, without the "5 second" delay or other predefined amount of delay needed to complete a pairing sequence. Users do not want a delay of several seconds when they press START and expect the stimulation to start right away.

If the fob detects that it has a low battery level, it saves the ID information, state and strength of the connected patch. This data is saved into nonvolatile memory in the fob. The power for the fob can then be fixed. The Fob can then immediately re-pair with the patch it used before, assumed still to be in range and on the user.

If the fob fails to pair with a patch, then the fob tries again. This is useful when a patch moves out of range of its fob. This is repeated, but the time between attempts increases slowly, to the point where the fob gives up. This saves power by reducing the number of "pings." If a ping is successful, then the fob checks the ID of that patch, and the patch checks the ID of the fob. If they are as remembered from the most recent paired condition, then the connection is reinstated.

As with pairing the fob to the patch, similar procedures can be used to pair beacon 114 to patch 120, and similar procedures can pair a smartphone or other host device to beacon 114 and/or patch 120.

Figure 8:
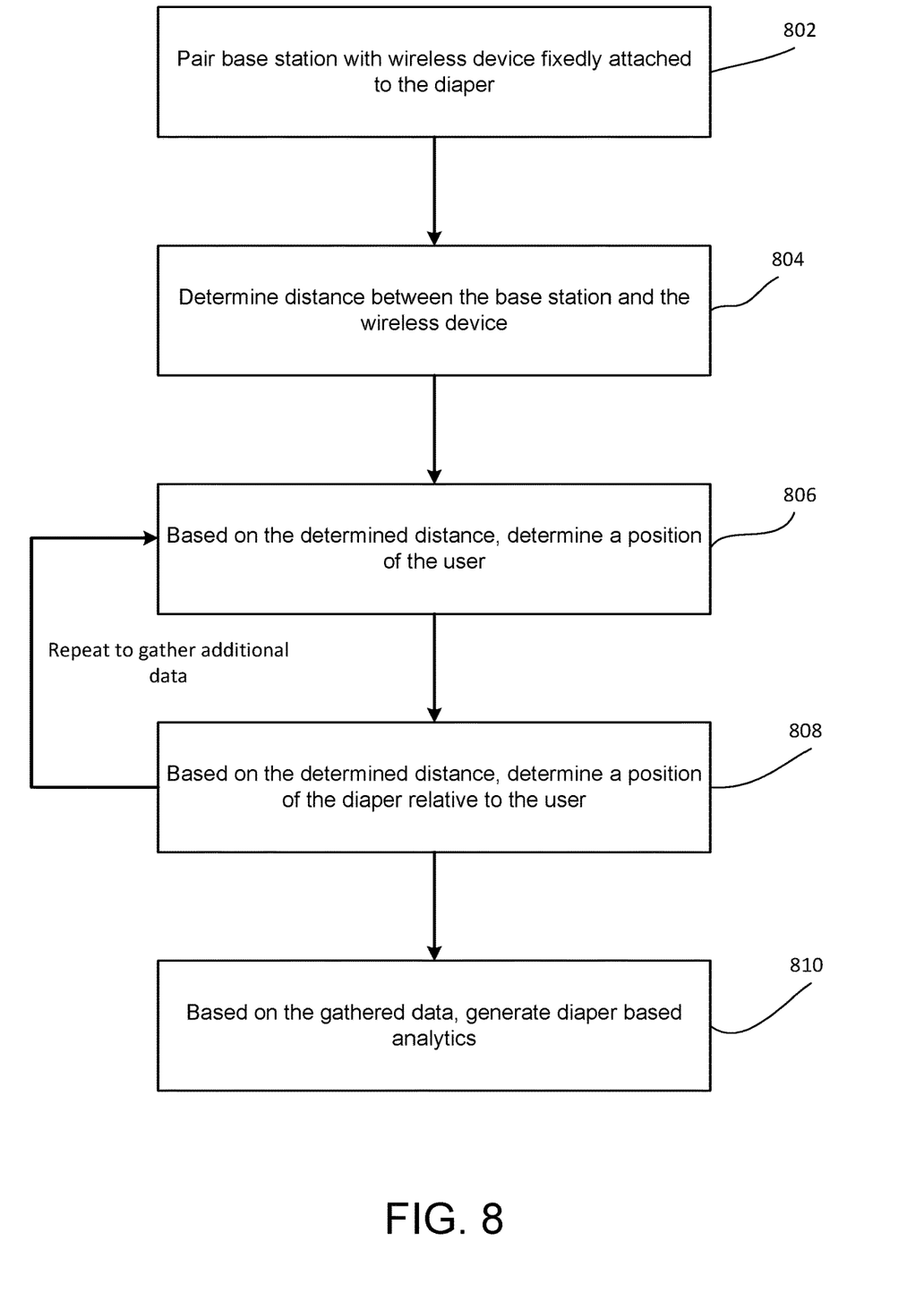
FIG. 8 is a flow diagram of the functionality of a base station and/or host device when determining smart diaper based data and analytics.

FIG. 8 is a flow diagram of the functionality of a base station and/or host device (e.g., patch 120, host device 140, base station 610) when determining smart diaper based data and analytics. In one example, the functionality of the flow diagram of FIG. 8 is implemented by software stored in memory or other computer readable or tangible medium, and executed by a processor. In other examples, the functionality may be performed by hardware (e.g., through the use of an application specific integrated circuit ("ASIC"), a programmable gate array ("PGA"), a field programmable gate array ("FPGA"), etc.), or any combination of hardware and software.

At 802, the base station is paired with the wireless beacon 114 or other wireless device fixedly attached to a diaper that is worn by a user.

At 804, a distance between the base station and wireless beacon 114 is determined.

At 806, based on the determined distance, a position/posture of the user may be determined. For example, determined positions may include standing, sitting, lying down, etc. For example, previous positions based on previously determined distances and that have been confirmed by the user are stored. The determined distance is then generally matched to previously determined distance (e.g., the closest to the current determined distance) and the corresponding previous position is selected.

At 808, based on the determined distance, a position of the diaper relative to the user is determined. For example, determined positions may include at the waist, on the thighs, at the knees, etc.

806 and/or 808 are repeated during a timeframe to gather additional data.

At 810, based on the gathered data, diaper based analytics are generated. The analytics can be based on additional data such as the geographic locations of the user, including movement history, the occurrence of bladder or bowel activity, and prior usage history of the user. Generated analytics can include one or more of: usage patterns of the diaper, a prediction of a next usage event, selection of type of next diaper depending on use case, ordering of additional diapers, determining alerts to be generated, user behavior, the posture of the user, a determination to stimulate nerves of the user to prevent a need to urinate, etc.

Several examples are specifically illustrated and/or described herein. However, it will be appreciated that modifications and variations of the disclosed examples are covered by the above teachings and within the purview of the appended claims without departing from the spirit and intended scope of the invention.

What is claimed is:

1. A smart diaper system comprising:
a diaper body adapted to be worn by a user;
an absorbent pad coupled to the diaper body;
a wireless communication device fixedly attached to the diaper body; and
a base station device in wireless communication with the wireless communication device, the base station device configured to determine a distance between the wireless communication device and the base station device, the base station device comprising a patch fixedly attached to the user.

2. The smart diaper system of claim 1, the wireless communication device comprising a wireless beacon.

3. The smart diaper system of claim 1, the diaper body comprising an integrated pocket, the wireless communication device inserted in the pocket.

4. The smart diaper system of claim 1, the base station device determining a position of the user based on the determined distance.

5. The smart diaper system of claim 4, the patch comprising a plurality of electrodes, the system repeating the determining the distance and determining the position of the user, storing a history of the distances and positions generated by the repeating; and
based on at least the history, the system initiating electrical stimuli via the electrodes to reduce an urge to urinate by the user.

6. The smart diaper system of claim 1, the base station device determining a position of the diaper body relative to the user based on the determined distance.

7. The smart diaper system of claim 1, further comprising a host device in wireless communication with the wireless communication device and the base station device.

8. The smart diaper system of claim 7, the host device comprising a smartphone or a fob.

9. A smart diaper comprising:
a diaper body adapted to be worn by a user;
an absorbent pad coupled to the diaper body; and
a wireless communication device fixedly attached to the diaper body, the wireless communication device in wireless communication with a base station device, the base station device configured to determine a distance between the wireless communication device and the base station device, the base station device comprising a patch fixedly attached to the user.

10. The smart diaper of claim 9, the wireless communication device comprising a wireless beacon.

11. The smart diaper of claim 9, the diaper body comprising an integrated pocket, the wireless communication device inserted in the pocket.

12. The smart diaper of claim 9, the base station device determining a position of the user based on the determined distance.

13. The smart diaper of claim 12, the patch comprising a plurality of electrodes, the base station device repeating the determining the distance and determining the position of the user, storing a history of the distances and positions generated by the repeating; and based on at least the history, the base station device initiating electrical stimuli via the electrodes to reduce an urge to urinate by the user.

14. The smart diaper of claim 9, the base station device determining a position of the diaper body relative to the user based on the determined distance.

15. The smart diaper of claim 9, the wireless communication device further in wireless communication with a host device.

16. The smart diaper of claim 15, the host device comprising a smartphone or a fob.

17. A method of monitoring diaper usage comprising:

determining a distance between a base station device and a wireless communication device fixedly attached to a diaper body of a diaper adapted to be worn by a user; and based on the determined distance, determining a position of the diaper body relative to the user and a position of the user.

18. The method of claim 17, wherein the determining the position of the user comprises:

storing previous positions of the user based on previous distances between the base station device and the wireless communication device, the previous positions of the user having been confirmed by the user; and generally matching the determined distance to one of the previous distances.

19. The method of claim 17, further comprising:

determining a type and quantity of additional diapers to order based on the determined distance.

20. The method of claim 17, the determined position of user comprising at least a sitting position or a non-sitting position.

21. The method of claim 17, the base station device comprising a patch fixedly attached to the user, the patch comprising a plurality of electrodes, the method further comprising:

repeating the determining the distance and determining the position of the diaper body relative to the user and the position of the user, storing a history of the distances and positions generated by the repeating; and based on at least the history, initiating electrical stimuli via the electrodes to reduce an urge to urinate by the user.

* * * * *